United States Patent
Shimazaki et al.

(10) Patent No.: US 9,228,987 B2
(45) Date of Patent: Jan. 5, 2016

(54) GAS SENSOR

(71) Applicant: NGK SPARK PLUG CO., LTD., Nagoya-shi, Aichi (JP)

(72) Inventors: Yuji Shimazaki, Kakamigahara (JP); Yasuhiro Fujita, Kaizu (JP); Takayoshi Atsumi, Kounan (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 318 days.

(21) Appl. No.: 13/914,840

(22) Filed: Jun. 11, 2013

(65) Prior Publication Data
US 2013/0327121 A1 Dec. 12, 2013

(30) Foreign Application Priority Data

Jun. 12, 2012 (JP) ................................ 2012-132517

(51) Int. Cl.
*G01N 27/409* (2006.01)
*G01N 33/00* (2006.01)
*G01N 27/407* (2006.01)

(52) U.S. Cl.
CPC ........ *G01N 33/0009* (2013.01); *G01N 27/4077* (2013.01)

(58) Field of Classification Search
CPC .......................... G01N 27/4077; G01N 33/009
USPC ................................ 73/23.31, 31.05; 204/428
See application file for complete search history.

(56) References Cited

U.S. PATENT DOCUMENTS

| 4,184,934 | A | * | 1/1980 | Bode et al. ..................... 204/428 |
| 4,199,424 | A | * | 4/1980 | Teitelbaum ..................... 204/428 |
| 4,505,807 | A | * | 3/1985 | Yamada ......................... 204/425 |
| 6,544,586 | B1 | | 4/2003 | Atsumi et al. |
| 7,007,543 | B2 | * | 3/2006 | Sakawa et al. ................ 73/23.32 |
| 7,758,736 | B2 | | 7/2010 | Okumura et al. |
| 7,810,375 | B2 | * | 10/2010 | Weyl et al. ..................... 73/23.31 |
| 7,901,556 | B2 | * | 3/2011 | Yamada ......................... 204/428 |
| 8,001,827 | B2 | * | 8/2011 | Weyl et al. ..................... 73/23.31 |
| 8,359,902 | B2 | * | 1/2013 | Thanigachalam et al. ... 73/23.31 |
| 8,479,561 | B2 | * | 7/2013 | Sekiya et al. ................. 73/31.05 |
| 2008/0067066 | A1 | | 3/2008 | Okumura et al. |

FOREIGN PATENT DOCUMENTS

| JP | 11-230930 A | 8/1999 |
| JP | 2008-096419 A | 4/2008 |
| JP | 2008-175685 A | 7/2008 |

* cited by examiner

*Primary Examiner* — Daniel S Larkin
(74) *Attorney, Agent, or Firm* — Sughrue Mion, PLLC

(57) ABSTRACT

A protector has a two-stage structure that includes a large-diameter portion and a small-diameter portion. The large-diameter portion includes a cylindrical first peripheral wall and a first front end wall. The small-diameter portion includes a cylindrical second peripheral wall connected to the first front end wall and a second front end wall connected to a front end portion of the second peripheral wall. Opening portions are not formed in the first and second peripheral walls. First opening portions, which are opened toward only first recessed portions and an inner surface of the first peripheral wall, are formed at the first front end wall. A second recessed portion and second opening portions, which are formed in the second recessed portion and are opened toward an inner surface of the second peripheral wall, are formed in the second front end wall.

7 Claims, 4 Drawing Sheets

GAS SENSOR

BACKGROUND OF THE INVENTION

1. Field of the Invention

The present invention relates to a gas sensor including a protector protecting a detecting element, which is exposed to a gas to be detected, from water.

2. Description of the Related Art

A gas sensor, such as an oxygen sensor, an NOX sensor, or an HC sensor, which detects a specific gas contained in an exhaust gas of an automobile or the like, is known in the art. An oxygen sensor, which is a typical gas sensor, includes a detecting element that includes a bottomed cylindrical solid electrolyte body made of a ceramic such as zirconia. A pair of electrodes is formed on the surfaces of the solid electrolyte body, the solid electrolyte body being interposed between the electrodes. When the gas sensor is used, a detecting electrode formed on the outer surface of the solid electrolyte body is exposed to the exhaust gas and a reference electrode formed on the inner surface of the solid electrolyte body is exposed to a reference gas (commonly, air). The detecting element detects oxygen contained in the exhaust gas by an electromotive force generated between the electrodes according to a difference in partial pressure of oxygen between two atmospheres isolated from each other by the solid electrolyte body, that is, between the exhaust gas and the reference gas.

Since this detecting element is not activated when the temperature is low, a heater heating the detecting element is provided near the detecting element. A heat generating resistor made of high melting point metal, such as tungsten or molybdenum, embedded in an insulating ceramic base body such as alumina, has been widely used as the heater. Since the heater is inserted into a cylindrical hole of the detecting element in use, the heater is formed in the shape of a round bar and the heat generating resistor is embedded into the front end portion of the heater. Further, electrode pads, which are used to supply current to the heat generating resistor, are disposed so as to be exposed to the outer surface of a rear end portion of the heater. Connection terminals, which are used to supply the current, are bonded to the electrode pads (for example, see JP-A-11-230930).

Furthermore, if moisture (water droplets) contained in an exhaust gas adheres to the detecting element (where the moisture, namely, water droplets contained in an exhaust gas wets the detecting element) when the temperature of the detecting element is high, there is a concern that cracks or breakage may occur on the detecting element due to thermal shock. For this reason, a protector covering the detecting element is mounted on the gas sensor, so that the detecting element is protected from water. For example, in each of gas sensors disclosed in JP-A-11-230930 and JP-A-2008-96419, a protector has a double structure that includes an inner protector covering a detecting element and an outer protector covering the inner protector. Outer introduction holes through which an exhaust gas is introduced into the outer protector are formed in the outer protector, and inner introduction holes where the exhaust gas introduced into the outer protector is introduced into a gas detecting chamber to which the detecting element is exposed are formed in the inner protector.

JP-A-2008-175685 is an example of the above-described related art.

3. Problems to be Solved by the Invention

However, in the gas sensor disclosed in JP-A-11-230930 or JP-A-2008-96419, the protector has a double structure that includes the outer protector and the inner protector. For this reason, the structure of the protector is complicated, so that many man-hours for assembly are required. Moreover, the cost of the protector is also increased.

SUMMARY OF THE INVENTION

The invention has been made to solve the above-described problems, and an object of the invention is to provide a gas sensor that can ensure water resistance similar to a protector having a double structure by a protector having a single structure.

The above object of the invention has been achieved by providing (1) a gas sensor having an axis, the gas sensor comprising a detecting element extending in the axial direction and including a detecting portion provided at a front end portion thereof and detecting a specific gas contained in a gas to be detected, a main metal fitting surrounding and holding the radial periphery of the detecting element in a state that the detecting portion protrudes from a front end portion of the main metal fitting; and a protector fixed to the front end portion of the main metal fitting and accommodating the detecting portion therein. The protector includes a large-diameter portion including a cylindrical first peripheral wall and a first front end wall connected to a front end portion of the first peripheral wall, a small-diameter portion connected to the first front end wall, protruding forward from the large-diameter portion in the axial direction, and including a cylindrical second peripheral wall connected to the first front end wall and a second front end wall connected to a front end portion of the second peripheral wall, first recessed portions formed at the first front end wall and recessed rearward in the axial direction, first opening portions formed at the first recessed portions and opened toward only an inner surface of the first peripheral wall, a second recessed portion formed at the second front end wall and recessed rearward in the axial direction, and second opening portions formed in the second recessed portion and opened toward an inner surface of the second peripheral wall so that the detecting element is not visible from the outside. Further, the first peripheral wall and the second peripheral wall are closed.

In the gas sensor (1) having this structure, the protector has a single structure that includes the large-diameter portion and the small-diameter portion protruding forward from the large-diameter portion. Accordingly, since the structure of the protector is simpler than the structure of a protector that has a double structure as in the related art, it is possible to reduce not only the man-hours for assembly but also the cost. Further, in the protector, opening portions are not formed in the first and second peripheral walls. Rather, the first opening portions and the second opening portions are formed in the first recessed portions of the first front end wall and the second recessed portion of the second front end wall, respectively. That is, openings of the protector are not formed in the flow direction of a gas to be detected that passes through a mounting target, and are formed in the direction crossing the flow direction of the gas to be detected. For this reason, since the gas to be detected does not reach the detecting element without a change of the flow direction where the gas to be detected flows in the mounting target, it is possible to suppress the adhesion of water droplets to the detecting element. Furthermore, the first opening portions are formed in the first recessed portions so as to be opened only toward the inner surface of the first peripheral wall. Accordingly, since water droplets adhere to the inner surface of the first peripheral wall even though the water droplets enter the protector from the first opening portions, it is possible to suppress the adhesion of the water droplets to the detecting element. On the other hand, the second opening portions are formed in the second recessed portion so as to be opened toward the inner surface of the second peripheral wall so that the detecting element cannot be viewed from the outside. Accordingly, since water droplets adhere to the inner surface of the second peripheral wall even though the water droplets enter the protector from the second opening portions, it is possible to suppress the adhesion of the water droplets to the detecting element.

In a preferred embodiment (2) of the gas sensor (1) above, the second peripheral wall has a cylindrical shape, the detecting element has a columnar shape, and an inner diameter of the second peripheral wall is larger than an outer diameter of the detecting element. In this case, since the first recessed portions and the first opening portions formed in the first front end wall are disposed outside the detecting element, it is possible to further suppress the adhesion of the water droplets, which have entered the protector from the first opening portions, to the detecting element.

In another preferred embodiment (3) of the gas sensor (1) or (2) above, the plurality of first opening portions are formed at the first front end wall at regular intervals along the first peripheral wall, and the second opening portions are opened toward a portion between the first opening portion and another first opening portion adjacent to the first opening portion when the protector is viewed along the axial line. In this case, the first and second opening portions are not opened in the same direction. Accordingly, when the gas sensor is disposed on the mounting target, the first opening portions and the second opening portions may be disposed so as not to be lined up on the upstream side of the gas to be detected. Accordingly, water droplets do not easily enter the protector.

In yet another preferred embodiment (4) of the gas sensor of any of (1) to (3) above, the first recessed portions has a dome shape where the first front end wall is pushed inward and other portions except for the first opening portions are connected to the first front end wall, and a portion of the first recessed portions close to the second peripheral wall smoothly continues to the outer surface of the second peripheral wall. In this case, when the gas to be detected colliding with the second peripheral wall reaches the first front end wall, the gas to be detected easily passes through the first recessed portions and is apt to flow into the protector from the first opening portions.

In yet another preferred embodiment (5) of the gas sensor of any of (1) to (4) above, the second recessed portion has two parallel cuts formed in the second front end wall and a portion between the two parallel cuts that is pushed inward, and portions corresponding to the two parallel cuts form the respective second opening portions. According to this structure, since water droplets adhere to the inner surface of the second peripheral wall even though water droplets enter the protector from the second opening portions, it is possible to suppress the adhesion of the water droplets to the detecting element.

In yet another preferred embodiment (6) of the gas sensor of any of (1) to (5) above, a hollow portion is formed in the detecting element, a heater, which heats the detecting element, is inserted into the hollow portion and contacts the detecting element at one position, and a direction facing the contact position between the heater and the detecting element from the axis is the same as a direction facing a portion between the first opening portion and another first opening portion adjacent to the first opening portion from the axis when the protector is viewed along the axis. In this case, the contact position of the detecting element with the heater, at which contact position temperature rises, does not face the first opening portions. Accordingly, even though some of water droplets having entered the protector from the first opening portions reach the detecting element, it is possible to suppress the occurrence of cracks or breakage on the detecting element.

In yet another preferred embodiment (7) of the gas sensor (6) above, the direction facing the contact position between the heater and the detecting element from the axis deviates from a direction facing the second opening portion from the axis. In this case, the contact position of the detecting element with the heater, at which contact position the temperature rises, does not face the second opening portions. Accordingly, even though some of water droplets having entered the protector from the second opening portions reach the detecting element, it is possible to suppress the occurrence of cracks or breakage on the detecting element.

DETAILED DESCRIPTION OF THE INVENTION

An embodiment of a gas sensor of the invention will be described below with reference to the drawings. However, the invention should not be construed as being limited thereto.

Figure 1:
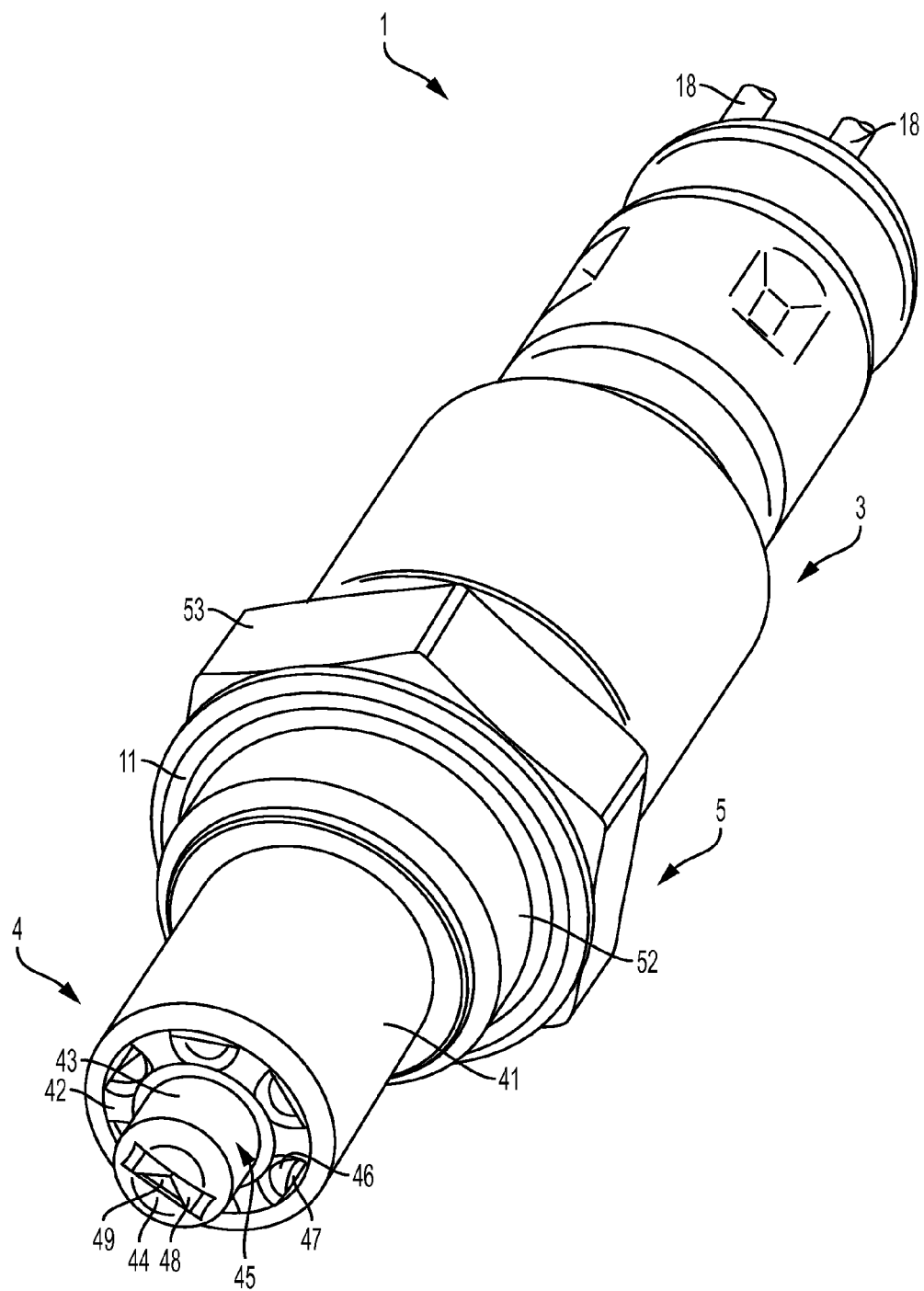
FIG. 1 is a perspective view of a gas sensor.

First, the structure of a gas sensor 1 including a detecting element 6 will be described with reference to FIGS. 1 and 2. When in use, the gas sensor 1 shown in FIG. 1 is mounted on an exhaust pipe (not shown) for an exhaust gas that is discharged from an internal combustion engine of an automobile or the like. In the following description, a side (which is a closed side and a lower side in the drawings) facing the front end of the detecting element 6, which is inserted into the exhaust pipe, in the direction of an axial line O of the gas sensor 1 is defined as a front end side or a lower side, and an opposite side (which is an upper side in the drawings) is defined as a rear end side or an upper side.

Figure 2:
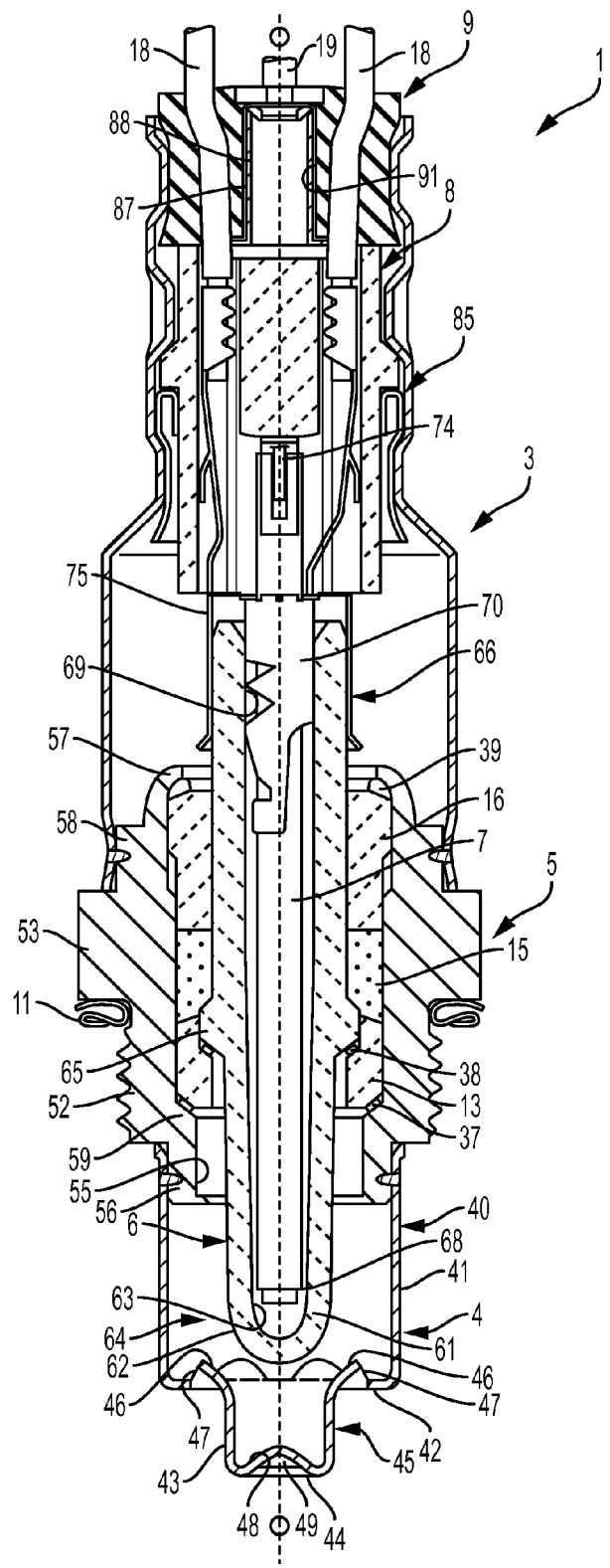
FIG. 2 is a longitudinal cross-sectional view of the gas sensor.

The gas sensor 1 shown in FIG. 2 is a sensor used to detect an oxygen concentration in an exhaust gas flowing in the exhaust pipe. The gas sensor 1 has a cylindrical detecting element 6, which is elongated and has a closed end, and which is surrounded and held by a main metal fitting 5.

The detecting element 6 contains zirconia as a main component, and includes a solid electrolyte body 61 that extends in the direction of the axial line O and is formed in a bottomed cylindrical shape. A flange-like flange portion 65, which protrudes outward in a radial direction, is provided at a substantially middle position of the solid electrolyte body 61 in the direction of the axial line O. The diameter of a front end portion 64, which is closer to the front end side than the flange portion 65, is gradually reduced toward the front end, and the front end portion of the detecting element 6 is closed in a spherical shape. Accordingly, a cylindrical hole 69 as a hollow portion is formed in the detecting element 6. A porous detecting electrode 62, which is made of Pt or a Pt alloy, is formed on the outer surface of the front end portion 64. Further, likewise, a porous reference electrode 63, which is made of Pt or a Pt alloy, is also formed on the inner surface of the cylindrical hole 69 of the solid electrolyte body 61. That is, the detecting electrode 62 and the reference electrode 63 face each other at the front end portion 64 with the solid electrolyte body 61 interposed therebetween. This portion functions as a detecting portion, which detects an oxygen concentration, of the detecting element 6. When the gas sensor 1 is mounted on an exhaust pipe (not shown) of an automobile, the front end portion 64 is exposed to an exhaust gas flowing in the exhaust pipe. Further, the detecting electrode 62 is covered with a protective layer (not shown) made of porous spinel, and is protected from poisoning caused by the exhaust gas.

As shown in FIG. 2, the detecting electrode 62 of the detecting element 6 is connected to a lead wire 18 that is electrically connected to an external circuit (not shown) (for example, an electronic control unit (ECU) of the automobile) through a connection terminal 75 fitted around a rear end portion 66 of the detecting element 6. Likewise, the reference electrode 63 of the detecting element 6 is connected to another lead wire 18 through a connection terminal 70 that is inserted into the cylindrical hole 69 of the detecting element 6. Furthermore, a bar-like heater 7, which activates the solid electrolyte body 61 by heating the solid electrolyte body 61, is inserted into the cylindrical hole 69 of the detecting element 6. The heater 7 is connected to a pair of lead wires 19 (only one lead wire 19 is shown in FIG. 2), which are electrically connected to the external circuit, through a pair of electrode terminals 74 bonded to electrodes that are exposed at the rear end thereof to supply current to a heat generating resistor (not shown) provided in the heater 7. Meanwhile, the heater 7 contacts the inner surface of the detecting element 6 at a contact position 68.

The detecting element 6 is held by the cylindrical main metal fitting 5 that is a metal fitting used to mount the gas sensor 1 on the exhaust pipe (not shown). Specifically, the main metal fitting 5 supports a support member 13 made of alumina, a filling member 15 made of talc powder, and a sleeve 16 made of alumina between a stepped portion 59, which is formed on a front end portion of a cylindrical hole 55, and a crimped portion 57, which is formed at a rear end of the cylindrical hole 55, by packings 37, 38 and 39. Further, since the flange portion 65 of the detecting element 6 is interposed between the support member 13 and the filling member 15, the detecting element 6 is held in the cylindrical hole 55 and airtightness in the cylindrical hole 55 is ensured by the filling member 15.

The main metal fitting 5 includes a male screw portion 52 that is formed on the outer periphery thereof and includes threads used to mount the gas sensor 1 on the exhaust pipe. A front end mounting portion 56 on which a protector 4, described below, is mounted is formed at the front end portion of the male screw portion 52. A tool engaging portion 53 with which a tool used to mount the gas sensor on the exhaust pipe is engaged is formed at the rear end portion of the male screw portion 52. An annular gasket 11, which prevents gas from leaking out from the mounting portion of the exhaust pipe, is fitted between the tool engaging portion 53 and the male screw portion 52. A rear end mounting portion 58 on which an outer cylinder 3, described below, is mounted is formed at the rear end portion of the tool engaging portion 53. The crimped portion 57 is formed at the rear end portion of the rear end mounting portion 58.

The rear end portion 66 of the detecting element 6 protrudes from the rear end (crimped portion 57) of the main metal fitting 5, and is covered with the outer cylinder 3 that is welded to the rear end mounting portion 58. The outer cylinder 3 is made of stainless steel such as SUS304 and is formed in the shape of a cylinder extending in the direction of the axial line O. The outer cylinder 3 is formed so that the diameter of a portion of the outer cylinder 3 close to the front end portion (lower portion in FIG. 2) from the substantially middle portion is larger than the diameter of the rear end portion of the outer cylinder 3. The rear end portion 66 of the detecting element 6, a separator 8, a grommet 9, and the like are disposed in the outer cylinder 3.

The cylindrical separator 8 made of an insulating ceramic is disposed on the rear end side of the rear end portion 66 of the detecting element 6 in the direction of the axial line O. The connection terminals 70 and 75 of the detecting element 6 and the electrode terminal 74 of the heater 7 are independently accommodated in the separator 8 so as not to come into contact with each other. Further, air can flow between the front and rear end portions of the separator 8 through gaps between the connection terminals 70 and 75 or the electrode terminal 74 and the inner peripheral surface of the separator 8. The outer periphery of a portion of the outer cylinder 3 where the separator 8 is disposed is crimped, so that the separator 8 is held in the outer cylinder 3 with a holding metal fitting 85 interposed therebetween.

The grommet 9 made of fluorine rubber is disposed on the rear end side of the separator 8. The grommet 9 is fitted to an opening formed at the rear end portion of the outer cylinder 3 and the outer periphery of the outer cylinder 3 near the opening is crimped, so that the grommet 9 is held by the outer cylinder 3. A communication hole 91 through which air is introduced into the outer cylinder 3 is formed in the grommet 9. A thin film-like filter member 87 made of a fluorine resin such as PTFE (polytetrafluoroethylene) and a fastener 88 thereof are inserted into the communication hole 91, so that the entry of water droplets or the like is prevented. Furthermore, the lead wires 18, which are connected to the connection terminals 70 and 75 in the separator 8, and the lead wires 19, which are connected to the electrode terminal 74, are led to the outside through the grommet 9.

A detecting portion of the front end portion 64 of the detecting element 6 protrudes from the front end mounting portion 56 of the main metal fitting 5, and is covered with the protector 4 that is welded to the front end mounting portion 56. The protector 4 protects the detecting portion of the detecting element 6, which protrudes into the exhaust pipe, from collision with water droplets or foreign material contained in an exhaust gas. The protector 4 has a single structure that includes an opening portion.

The details of the structure of the protector 4 will be described below with reference to FIGS. 1 to 4. The protector 4 includes a cylindrical large-diameter portion 40 and a cylindrical small-diameter portion 45 of which the outer diameter is smaller than the outer diameter of the large-diameter portion 40. Accordingly, the protector 4 has a two-stage structure that includes a large-diameter portion 40 and a small-diameter portion 45. The large-diameter portion 40 includes a cylindrical first peripheral wall 41 and a first front end wall 42 that is connected to the front end portion of the first peripheral wall 41. The small-diameter portion 45 is connected to the first front end wall 42 and protrudes forward from the large-diameter portion 40 in the direction of the axial line O. The small-diameter portion 45 includes a cylindrical second peripheral wall 43 that is connected to the first front end wall 42 and a second front end wall 44 that is connected to the front end portion of the second peripheral wall 43. Meanwhile, the inner diameter of the second peripheral wall 43 is larger than the outer diameter of the front end portion 64 of the detecting element 6. Further, the first and second peripheral walls 41 and 43 are closed without an opening portion.

First recessed portions 46, which are recessed rearward in the direction of the axial line O, and first opening portions 47, which are formed at the first recessed portions 46 and opened toward only the inner surface of the first peripheral wall 41, are formed at the first front end wall 42. An exhaust gas is introduced into the protector 4 from the first opening portions 47. The first recessed portions 46 and the first opening portions 47 are formed at the first front end wall 42 at regular intervals along the first peripheral wall 41. In this embodiment, six first recessed portions 46 and six first opening portions 47 are formed at regular intervals by way of example.

Figure 4:
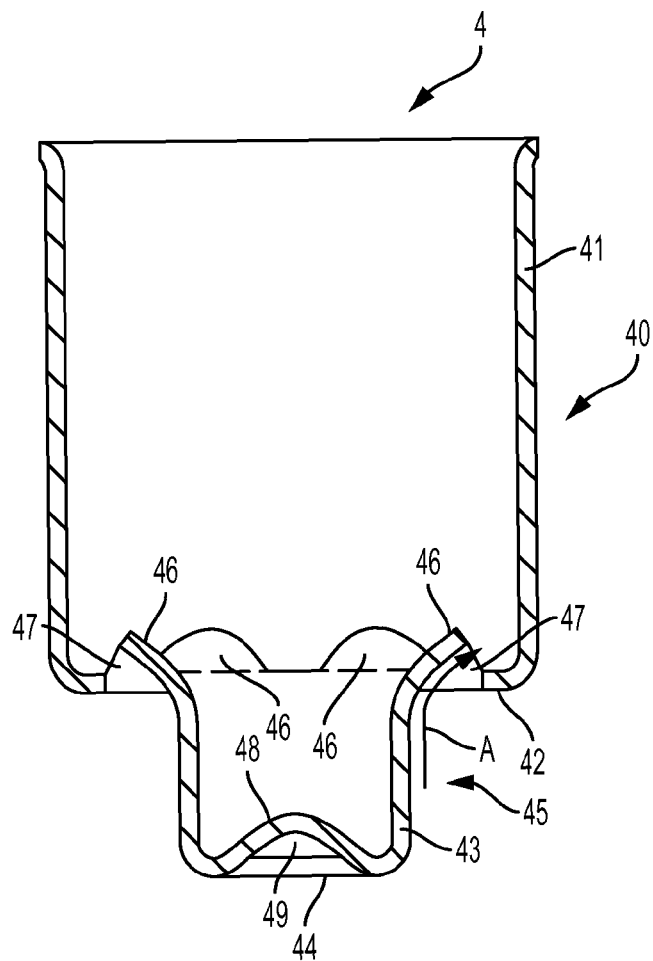
FIG. 4 is a longitudinal cross-sectional view of the protector when viewed in the same direction as in FIG. 2.

The first recessed portions 46 have a dome shape where the first front end wall 42 is pushed inward (toward the front end portion 64 of the detecting element 6) and other portions except for the first opening portions 47 are connected to the first front end wall 42. As shown in FIG. 4, a portion of the first recessed portions 46 close to the second peripheral wall 43 is formed so as to smoothly continue to the outer surface of the second peripheral wall 43. Accordingly, when an exhaust gas colliding with the second peripheral wall 43 reaches the first front end wall 42, the exhaust gas is apt to smoothly flow into the protector 4 as shown by an arrow A of FIG. 4.

Figure 3:
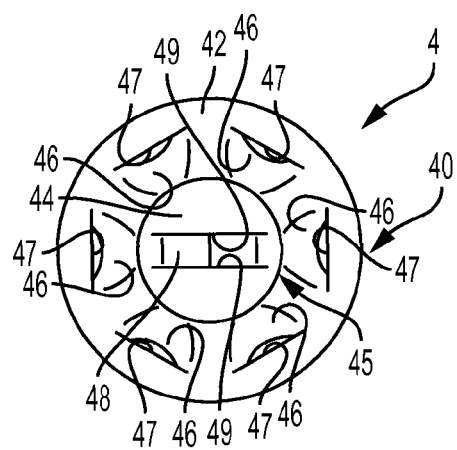
FIG. 3 is a bottom view of a protector of the gas sensor.

Further, the second front end wall 44 is provided with a second recessed portion 48 that is recessed rearward in the direction of the axial line O. Further, second opening portions 49 that are formed in the second recessed portion 48 are opened toward the inner surface of the second peripheral wall 43 so that the detecting element 6 (see FIG. 2) cannot be viewed from the outside. The second opening portions 49 are outlets through which water droplets or an exhaust gas entering the protector is discharged to the outside. As shown in FIG. 3, the second recessed portion 48 is formed in a shape where two parallel cuts are formed in the second front end wall 44 and a portion between the two parallel cuts is pushed inward, and portions corresponding to the two parallel cuts form the respective second opening portions 49 and 49. When the protector 4 is viewed along the axial line O (see FIG. 2), the second opening portion 49 is opened toward a portion between the first opening portion 47 and another first opening portion 47 adjacent to the first opening portion 47 as shown in FIG. 3.

Figure 5:
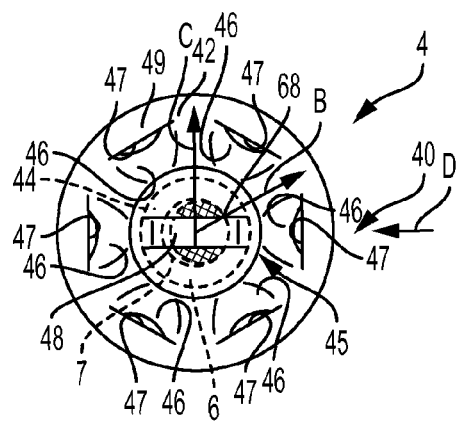
FIG. 5 is a bottom view of the protector showing a flow direction of an exhaust gas and a rotational angle of the mounted gas sensor.

Furthermore, when the protector 4 is viewed along the axial line O (see FIG. 2), a direction (an arrow B of FIG. 5) facing the contact position 68 between the heater 7 (see FIG. 2) and the detecting element 6 from the axial line O is the same as a direction (the arrow B of FIG. 5) facing a portion between the first opening portion 47 and another first opening portion 47 adjacent to the first opening portion 47 from the axial line O as shown in FIG. 5. Moreover, the direction (the arrow B of FIG. 5) facing the contact position 68 between the heater 7 (see FIG. 2) and the detecting element 6 from the axial line O deviates from a direction (an arrow C of FIG. 5) facing the second opening portion 49 from the axial line O.

As described above, in the gas sensor 1 of this embodiment, the protector 4 has a single structure that includes the large-diameter portion 40 and the small-diameter portion 45. Accordingly, since the structure of the protector is simpler than the structure of a protector that has a double structure as in the related art, it is possible to reduce not only man-hours for assembly but also cost. Further, in the protector 4, opening portions are not formed in the first and second peripheral walls 41 and 43. Further, the first opening portions 47 and the second opening portions 49 are formed in the first recessed portions 46 of the first front end wall 42 and the second recessed portion 48 of the second front end wall 44, respectively. That is, the openings of the protector 4 are not formed in the flow direction of an exhaust gas (a radial direction perpendicular to the direction of the axial line O), and are formed in the direction (the direction of the axial line O) crossing the flow direction of the exhaust gas. For this reason, since exhaust gas does not reach the detecting element 6 without a change in the flow direction thereof, it is possible to suppress the adhesion of water droplets to the detecting element 6. Furthermore, the first opening portions 47 are formed in the first recessed portions 46 so as to open toward only the inner surface of the first peripheral wall 41. Accordingly, since water droplets adhere to the inner surface of the first peripheral wall 41 even though entering the protector from the first opening portions 47, it is possible to suppress adhesion of the water droplets to the front end portion 64 of the detecting element 6. On the other hand, the second opening portions 49 are formed in the second recessed portion 48 so as to open toward the inner surface of the second peripheral wall 43 such that the detecting element 6 cannot be seen from the outside. Accordingly, since water droplets adhere to the inner surface of the second peripheral wall 43 even though the water droplets enter the protector from the second opening portions 49, it is possible to suppress the adhesion of water droplets to the detecting element.

Moreover, the second peripheral wall 43 is formed in a cylindrical shape, the detecting element 6 is formed in a columnar shape, and the inner diameter of the second peripheral wall 43 is larger than the outer diameter of the detecting element 6. In this case, since the first recessed portions 46 and the first opening portions 47 formed in the first front end wall 42 are disposed outside the detecting element 6 in the radial direction, it is possible to further suppress the adhesion of water droplets, which have entered the protector from the first opening portions 47, to the detecting element 6.

Further, when the protector 4 is viewed along the axial line O (see FIG. 2), the second opening portions 49 are opened toward a portion between the first opening portion 47 and another first opening portion 47 adjacent to the first opening portion 47. In this case, when the gas sensor is disposed on the exhaust pipe so that the opening direction of the first opening portion 47 is not the same as the opening direction of the second opening portion 49, the first opening portions 47 and the second opening portions 49 are disposed so as not to be lined up on the upstream side of an exhaust gas. Accordingly, water droplets do not easily enter the protector 4.

Figure 6:
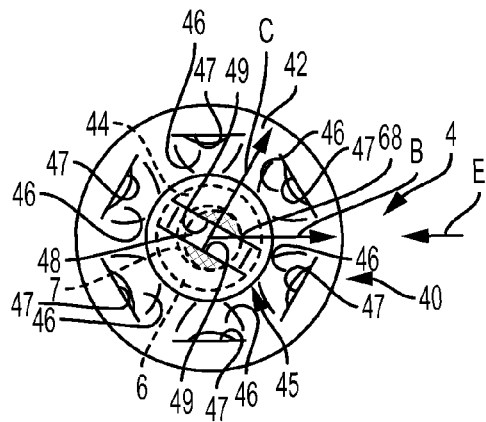
FIG. 6 is a bottom view of the protector showing a flow direction of an exhaust gas and a rotational angle of the mounted gas sensor.
Figure 7:
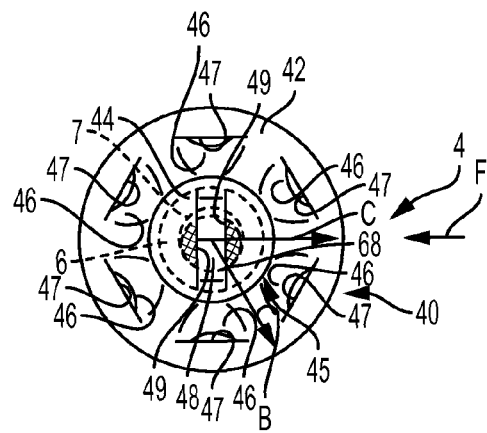
FIG. 7 is a bottom view of the protector showing a flow direction of an exhaust gas and a rotational angle of the mounted gas sensor.

For example, when the gas sensor 1 is fixed to the exhaust pipe at a rotational angle shown in FIG. 5 so that an exhaust gas flows in the direction of an arrow D, the first opening portions 47 are positioned in the direction of the arrow D but the second opening portions 49 face the direction of the arrow C. Accordingly, the first opening portions 47 and the second opening portions 49 are disposed so as not to be lined up in the direction of the arrow D. Consequently, water droplets do not easily enter the protector 4. Furthermore, even when the gas sensor 1 is fixed to the exhaust pipe at a rotational angle shown in FIG. 6 or 7 so that an exhaust gas flows in the direction of an arrow E shown in FIG. 6 or in the direction of an arrow F shown in FIG. 7, the first opening portions 47 and the second opening portions 49 are disposed so as not to be lined up in the directions of the arrows E and F as in FIG. 5. In FIG. 6, both the first opening portions 47 and the second opening portions 49 are not disposed in the direction of the arrow E. Further, in FIG. 7, the second opening portions 49 are disposed in the direction of the arrow F but the first opening portions 47 are not disposed in the direction of the arrow F. Accordingly, water droplets do not easily enter the protector 4.

Moreover, when the protector 4 is viewed along the axial line O (see FIG. 2), the direction (the arrow B of FIG. 5) facing the contact position 68 between the heater 7 (see FIG. 2) and the detecting element 6 from the axial line O faces a portion between the first opening portion 47 and another first opening portion 47 adjacent to the first opening portion 47. Accordingly, the contact position 68 of the detecting element 6 where temperature rises does not face the first opening portions 47. Accordingly, even though some of water droplets having entered the protector from the first opening portions 47 reach the detecting element 6, it is possible to suppress the occurrence of cracks or breakage of the detecting element 6. Further, when the protector 4 is viewed along the axial line O (see FIG. 2), the direction (the arrow B of FIG. 5) facing the contact position 68 between the heater 7 (see FIG. 2) and the detecting element 6 from the axial line O is not the same as the direction (the arrow C of FIG. 5) facing the second opening portion 49 from the axial line O and deviates from the direction (the arrow C of FIG. 5) facing the second opening portion 49 from the axial line O. Accordingly, even though some of water droplets having entered the protector from the second opening portions 49 reach the detecting element 6, it is possible to suppress the occurrence of cracks or breakage of the detecting element 6.

The invention has been described in detail with reference to the above embodiments. However, the invention should not be construed as being limited thereto. For example, each of the number of the first recessed portions 46 and the number of the first opening portions 47 is not limited to six, and may be arbitrary, such as five or eight. It should further be apparent to those skilled in the art that various changes in form and detail of the invention as shown and described above may be made. It is intended that such changes be included within the spirit and scope of the claims appended hereto.

This application is based on Japanese Patent Application No. JP 2012-132517 filed Jun. 12, 2012, incorporated herein by reference in its entirety.

What is claimed is:

1. A gas sensor having an axis, the gas sensor comprising:
    a detecting element extending in the axial direction and including a detecting portion provided at a front end portion thereof and detecting a specific gas contained in a gas to be detected;
    a main metal fitting surrounding and holding the radial periphery of the detecting element in a state that the detecting portion protrudes from a front end portion of the main metal fitting; and
    a protector fixed to the front end portion of the main metal fitting and accommodating the detecting portion therein,
    wherein the protector includes
        a large-diameter portion including a cylindrical first peripheral wall and a first front end wall connected to a front end portion of the first peripheral wall,
        a small-diameter portion connected to the first front end wall, protruding forward from the large-diameter portion in the axial direction, and including a cylindrical second peripheral wall connected to the first front end wall and a second front end wall connected to a front end portion of the second peripheral wall,
        first recessed portions formed at the first front end wall and recessed rearward in the axial direction,
        first opening portions formed at the first recessed portions and opened toward only an inner surface of the first peripheral wall,
        a second recessed portion formed at the second front end wall and recessed rearward in the axial direction, and
        second opening portions formed in the second recessed portion and opened toward an inner surface of the second peripheral wall so that the detecting element is not visible from the outside, and
    the first peripheral wall and the second peripheral wall are closed.

2. The gas sensor as claimed in claim 1,
    wherein the second peripheral wall has a cylindrical shape, the detecting element has a columnar shape, and
    an inner diameter of the second peripheral wall is larger than an outer diameter of the detecting element.

3. The gas sensor as claimed in claim 1,
    wherein the plurality of first opening portions are formed at the first front end wall at regular intervals along the first peripheral wall, and
    the second opening portions are opened toward a portion between the first opening portion and another first opening portion adjacent to the first opening portion when the protector is viewed along the axial direction.

4. The gas sensor as claimed in claim 1,
    wherein the first recessed portions have a dome shape where the first front end wall is pushed inward and other portions except for the first opening portions are connected to the first front end wall, and
    a portion of the first recessed portions close to the second peripheral wall smoothly continues to the outer surface of the second peripheral wall.

5. The gas sensor as claimed in claim 1,
    wherein the second recessed portion has two parallel cuts formed in the second front end wall and a portion between the two parallel cuts that is pushed inward, and
    portions corresponding to the two parallel cuts form the respective second opening portions.

6. The gas sensor as claimed in claim 1,
    wherein a hollow portion is formed in the detecting element,
    a heater, which heats the detecting element, is inserted into the hollow portion and contacts the detecting element at one position, and
    a direction facing the contact position between the heater and the detecting element from the axis is the same as a direction facing a portion between the first opening portion and another first opening portion adjacent to the first opening portion from the axis when the protector is viewed along the axis.

7. The gas sensor as claimed in claim 6,
    wherein the direction facing the contact position between the heater and the detecting element from the axis deviates from a direction facing the second opening portion from the axis.

* * * * *